United States Patent
Chen et al.

(10) Patent No.: US 6,849,074 B2
(45) Date of Patent: Feb. 1, 2005

(54) DISPOSABLE SURGICAL DEVICES

(75) Inventors: Paul Fei-Ta Chen, Sunnyvale, CA (US); James John Levante, Redwood City, CA (US); Chuong Dinh Nguyen, Sunnyvale, CA (US)

(73) Assignee: Medconx, Inc., Santa Clara, CA (US)

( * ) Notice: Subject to any disclaimer, the term of this patent is extended or adjusted under 35 U.S.C. 154(b) by 167 days.

(21) Appl. No.: 10/171,698

(22) Filed: Jun. 17, 2002

(65) Prior Publication Data

US 2003/0233087 A1 Dec. 18, 2003

(51) Int. Cl.[7] .............................................. A61B 18/18
(52) U.S. Cl. ...................................................... 606/41
(58) Field of Search ........................ 606/27–31, 32–52

(56) References Cited

U.S. PATENT DOCUMENTS

| | | | |
|---|---|---|---|
| 5,599,348 A | * | 2/1997 | Gentelia et al. ............... 606/45 |
| 6,102,907 A | * | 8/2000 | Smethers et al. ............. 606/40 |
| 6,165,173 A | * | 12/2000 | Kamdar et al. ............... 606/34 |
| 6,296,636 B1 | * | 10/2001 | Cheng et al. .................. 606/32 |
| 6,511,478 B1 | * | 1/2003 | Burnside et al. .............. 606/41 |

* cited by examiner

*Primary Examiner*—Roy D. Gibson
*Assistant Examiner*—Pete Vrettakos
(74) *Attorney, Agent, or Firm*—Burns, Doane, Swecker & Mathis, LLP (57) ABSTRACT

A disposable surgical device is constructed to include a shell, a smart block mounted in one end of the shell, the smart block electronic having components mounted to a circuit embedded therein, front contact pins for insertion into respective contact holes in the connector of an industry standard connector interface, and rear wire terminal points, a medical treatment terminal installed in the other side of the shell and adapted for performing surgery and treatments, and a flex circuit termination electrically connected between the smart block and the medical treatment terminal, the flex circuit termination having embedded conductor lines respectively connected to the medical treatment terminal and wire terminal points at the ends of the conductor lines respectively soldered to the wire terminal points of the smart block.

13 Claims, 8 Drawing Sheets

DISPOSABLE SURGICAL DEVICES

BACKGROUND OF THE INVENTION

1. Field of the Invention

The present invention relates to disposable surgical devices for use with a medical apparatus to perform invasive surgery and treatments and, more particularly, to such disposable surgical devices that are easy and inexpensive to manufacture.

2. Description of the Related Art

Figure 10:
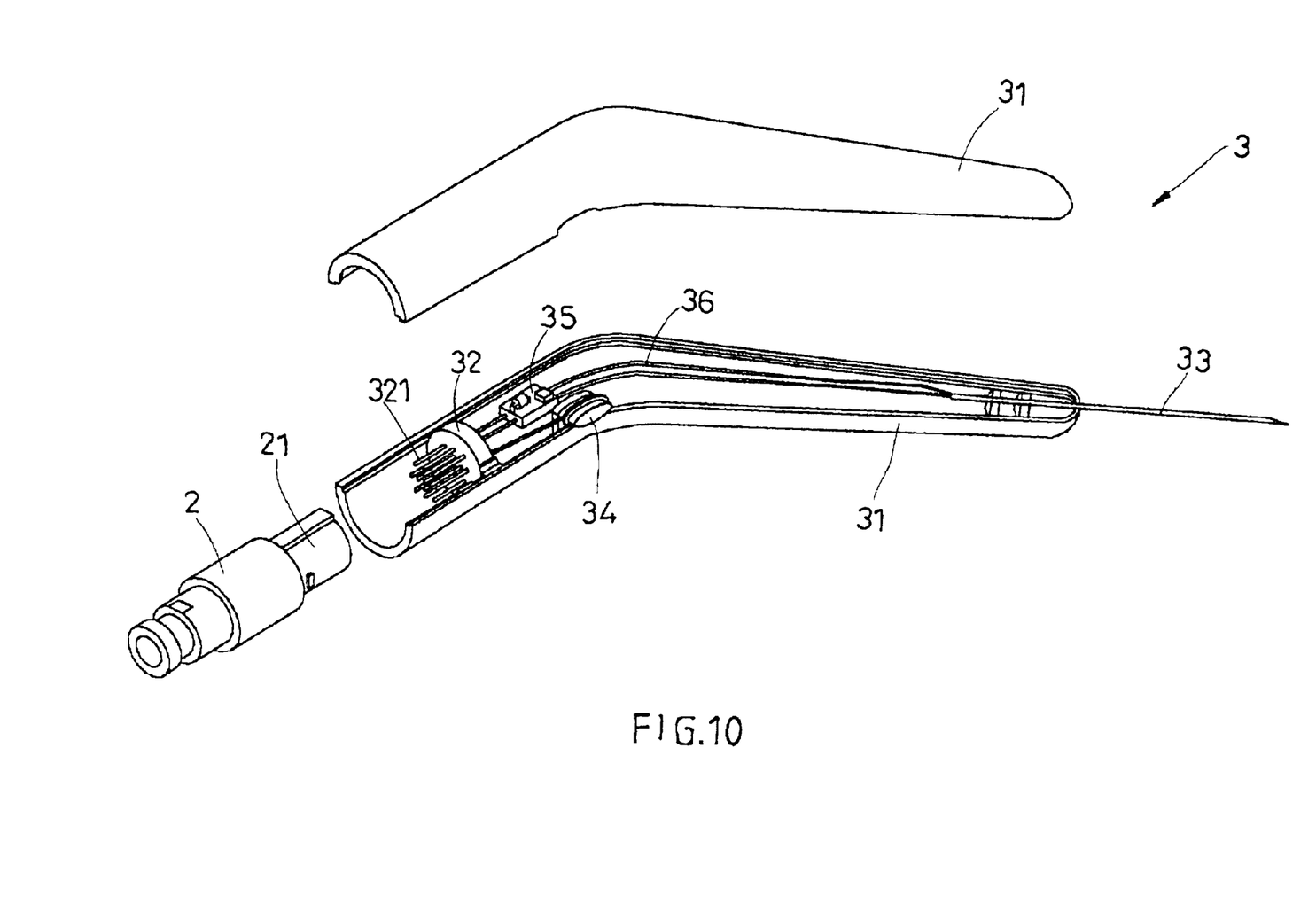
FIG. 10 is an exploded view of a disposable surgical device according to the prior art.
Figure 11:
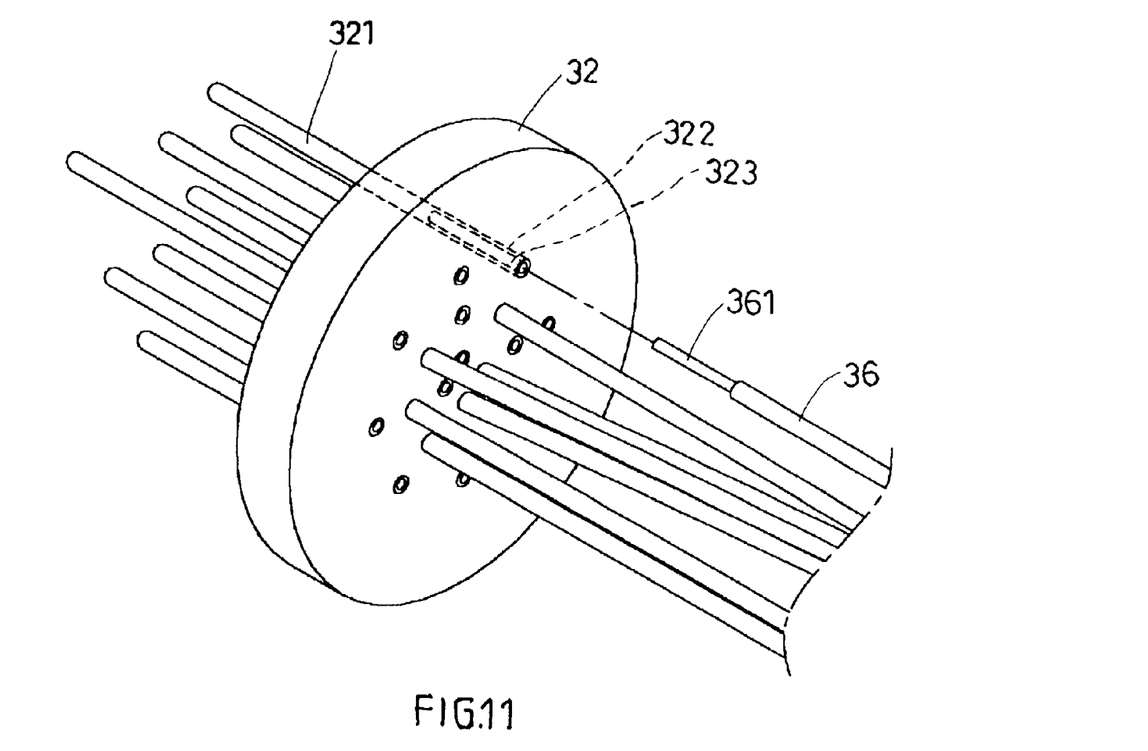
FIG. 11 is a perspective view of the connection block for the disposable surgical device according to the prior art.
Figure 12:
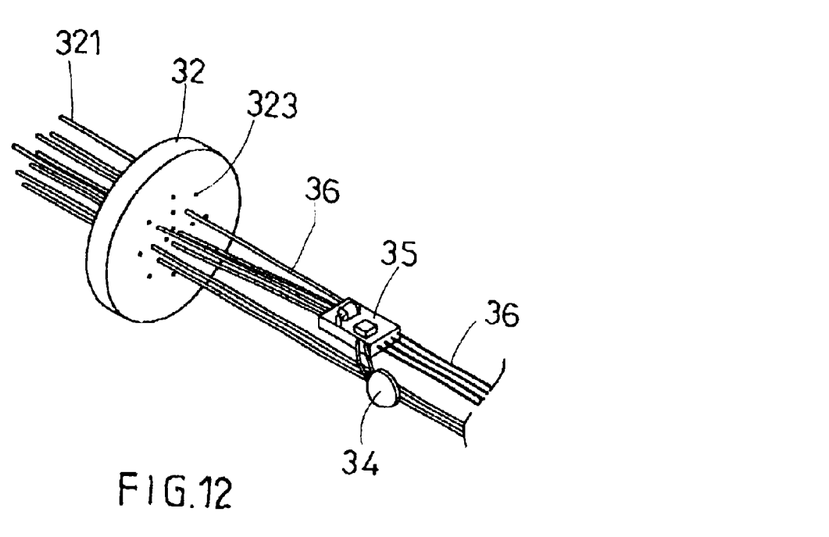
FIG. 12 is a perspective view of a part of the prior art disposable surgical device, showing the circuit board connected to the connection block.

The medical industry uses RF energy to perform invasive surgery and treatments. These procedures are performed through the use of disposable surgical devices. FIGS. 10~12 show a prior art disposable surgical device 3 for this purpose. This structure of disposable surgical device 3 comprises a shell (housing) 31, a connection block 32, a medical treatment terminal, for example, a surgical tip 33, a switch 34, a circuit board 35, and electric wires 36 connecting the parts. The connection block 32 comprises a plurality of forwardly extended contact pins 231 for connecting to an industry standard connector interface 2. The contact pins 231 each have a tubular rear end 322 extended to the rear side of the connecting block 32 and defining a respective solder hole 323 for the connection of the conductors 361 of the electric wires 36. This structure of disposable surgical device 3 has numerous drawbacks as outlined hereinafter:

1. During fabrication, the conductors 361 of the electric wires 36 must be respectively individually inserted into the solder holes 323 of the contact pins 231 and then soldered thereto by a soldering apparatus. This assembly process is time consuming and costly.
2. The installation of the circuit board 35 in the electric wires 36 is time and labor consuming, resulting in high manufacturing cost.
3. It requires skilled person to solder the electric wires 36 to respective wire terminal points. The manual assembly of the components can lead to quality issues.

SUMMARY OF THE INVENTION

The present invention has been accomplished to provide disposable surgical devices, which eliminate the aforesaid drawbacks. It is therefore the main object of the present invention to provide disposable surgical devices, which consume less time and labor. It is another object of the present invention to provide disposable surgical devices, which are easy and inexpensive to manufacture. It is still another object of the present invention to provide a smart block technology to combine the major component requirements of disposable surgical devices into a single connector interface. It is still another object of the present invention to provide a smart block for disposable surgical devices, which is machine built and provides a solderless termination for solid discrete wires, or solder terminations for stranded wires and flex circuits. It is still another object of the present invention to provide a smart block for disposable surgical devices, which can be configured to tie pins together and mount active and passive electronic components around and between pins. It is still another object of the present invention to provide a smart block for disposable surgical devices, which eliminates the need for the hand mounting of components and PCB thus eliminating quality issues pertaining to this effort like wire shorting, poor solder joints and broken wires.

DETAILED DESCRIPTION OF THE PREFERRED EMBODIMENT

Referring to FIGS. from 1 through 4, a disposable surgical device 1 in accordance with a first embodiment of the present invention is shown comprised of a shell (housing) 11, a smart block 12, an industry standard socket 13, a medical treatment terminal, for example, a surgical tip 14, and a flex circuit termination 15 connected between the smart block 12 and the surgical tip 14. The smart block 12 is provided inside the shell 11 near its rear end, having a circuit 121 embedded therein and electronic components 122 mounted to the circuit 121 subject to the surgery or treatments to be performed. A plurality of metal contact pins 123 are provided at one side of the smart block 12 for insertion into respective contact holes 221 in the connector 22 in the plug end 21 of an industry standard connector interface 2 to electrically connect the industry standard connector interface 2 to the circuit 121 of the smart block 12. The smart block 12 further comprises a plurality of wire terminal points (solder points) 124 provided at the other side opposite to the contact pins 123. By means of the aforesaid arrangement, the smart block 12 serves as a circuit board as well as receptacle means to receive the industry standard connector interface 2. The flex circuit termination 15 comprises a plurality of conductor (copper foil) lines 151 and wire terminal points (solder points) (not shown) at the ends of the conductor lines 151 corresponding to the wire terminal points (solder points) 124 of the smart block 12. By means of the application of a soldering equipment, the wire terminal points (solder points) of the conductor lines 151 of the flex circuit termination 15 are respectively soldered to the wire terminal points (solder points) 124 of the smart block 12 rapidly and efficiently with less labor and time. Further, the desired circuit 121 and electronic components 122 are mounted to the smart block 12 subject to the surgery or treatments to be performed during the fabrication of the smart block 12. Because the wire terminal points (solder points) 124 of the smart block 12 are respectively soldered to the respective wire terminal points (solder points) of the conductor lines 151 of the flex circuit termination 15 at a time and the metal contact pins 123 of the smart block 12 are directly inserted into the contact holes 221 in the connector 22 in the plug end 21 of the industry standard connector interface 2 to achieve the connection, the manufacturing process of the present invention is efficient. Further, electronic components such as capacitor 152, resistor, power on/off switch 16, status indicator light 17, and etc., are directly mounted to the flex circuit termination 15 during the fabrication of the disposable surgical device 1 to simplify the manufacturing process and to relatively reduce the manufacturing cost. The industry standard socket 13 is provided in one end, namely, the rear end of the shell 11, comprising a socket hole 131 disposed in the front side thereof and adapted for receiving the plug end 21 of the industry standard connector interface 2, two retaining lugs 133 bilaterally backwardly extended from the rear side 132 thereof and terminating in a respective hooked portion 134 adapted for hooking in a respective retaining notch 125 in the smart block 12 to secure the smart block 12 to the industry standard socket 13.

Figure 1:
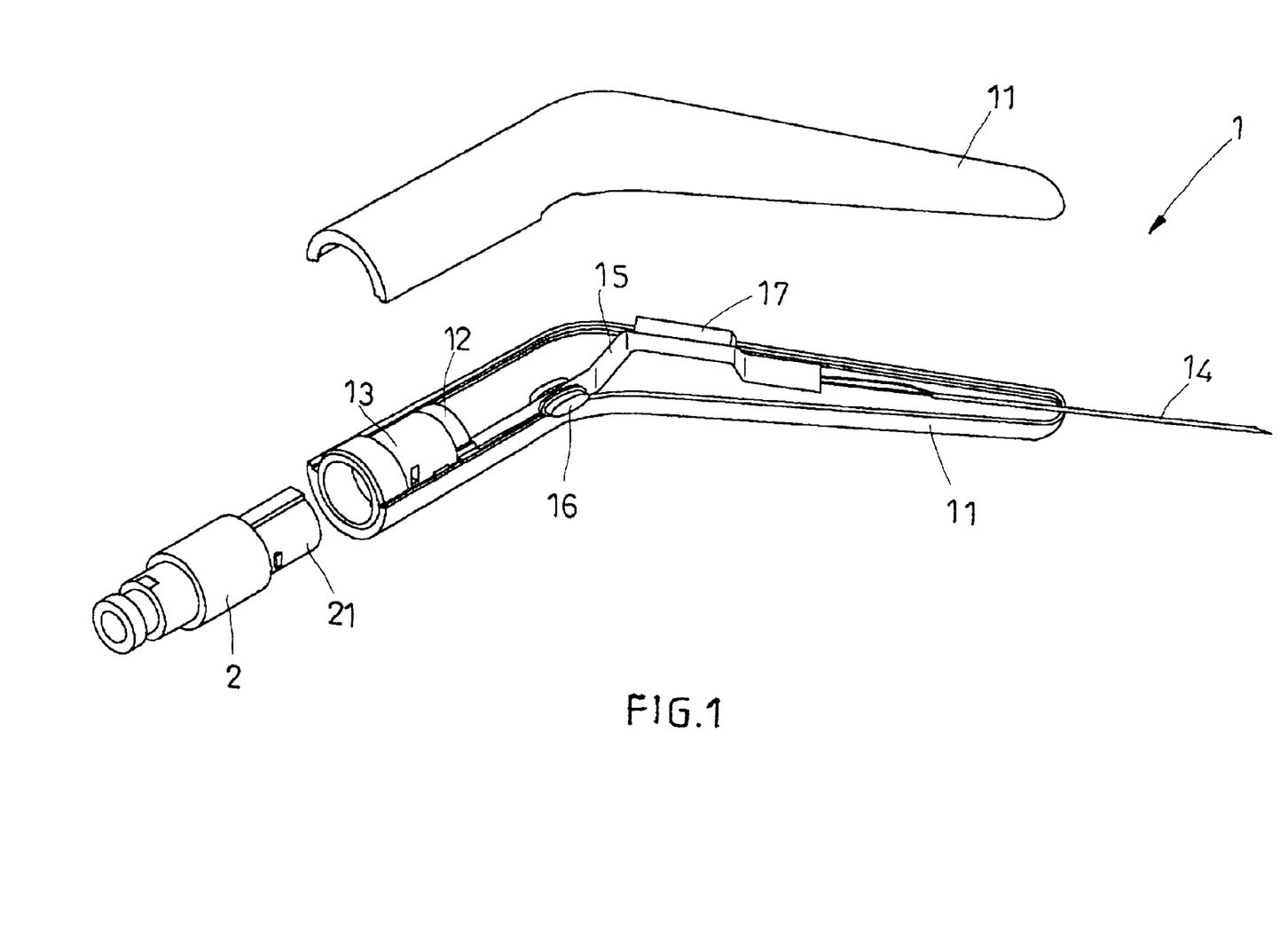
FIG. 1 is an exploded view of a disposable surgical device according to a first embodiment of the present invention.
Figure 2:
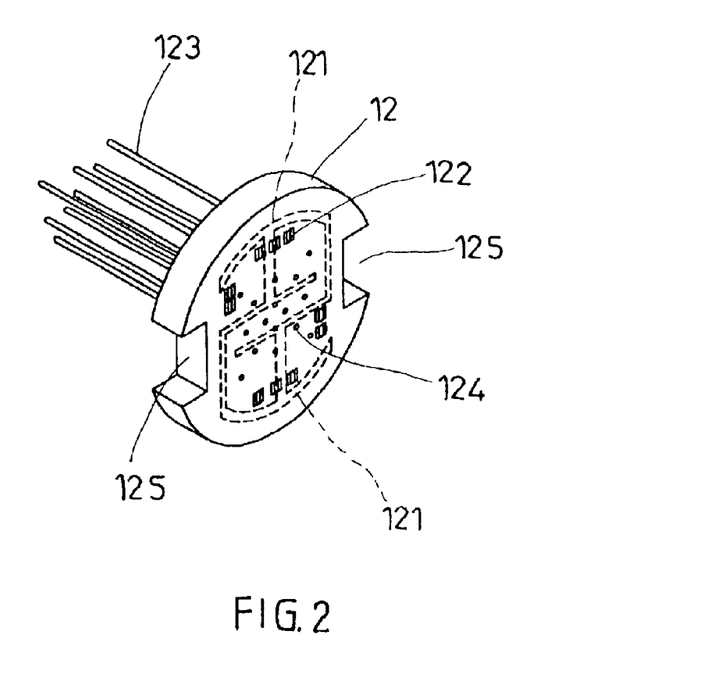
FIG. 2 is a perspective view of the smart block for the disposable surgical device according to the first embodiment of the present invention.
Figures 3, 4:
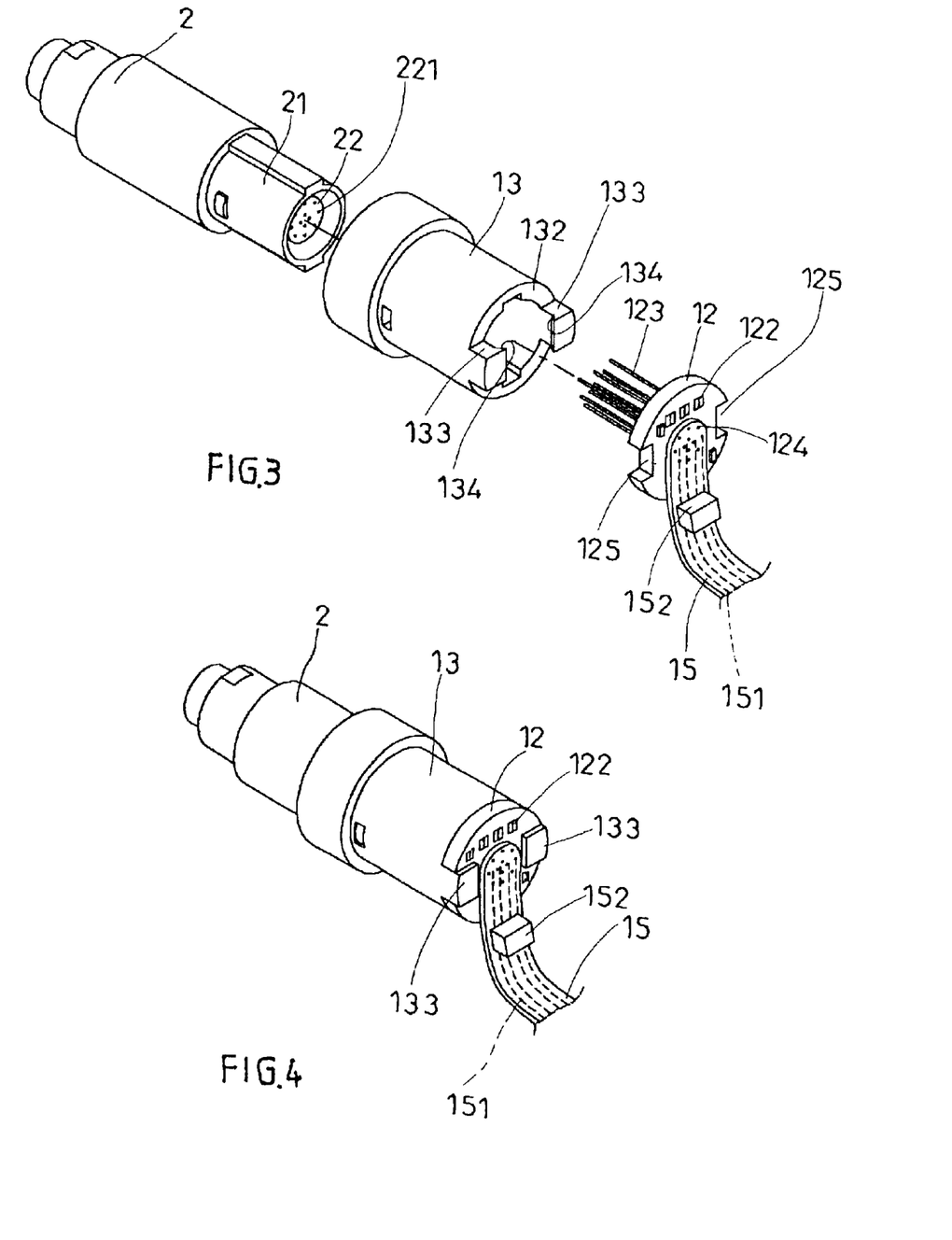
FIG. 3 is an exploded view of a part of the present invention, showing the relative positioning of the socket between the smart block and the industry standard connector interface.
FIG. 4 is an assembly view of FIG. 3.
Figure 5:
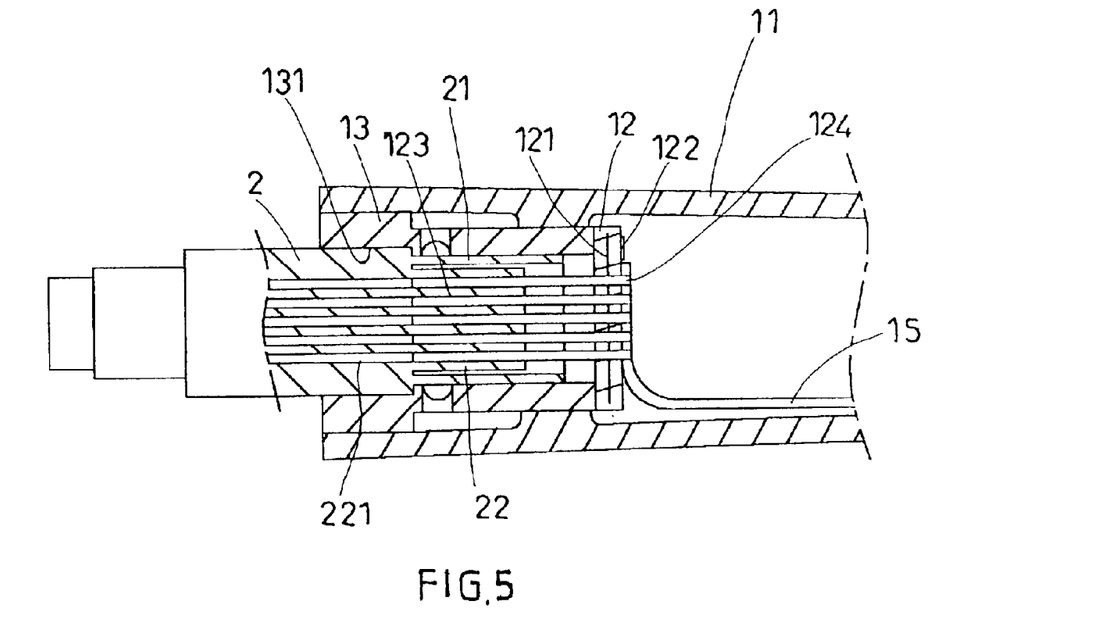
FIG. 5 is a sectional view of a part of the present invention, showing the industry standard connector interface inserted into the socket and connected to the smart block.
Figure 6:
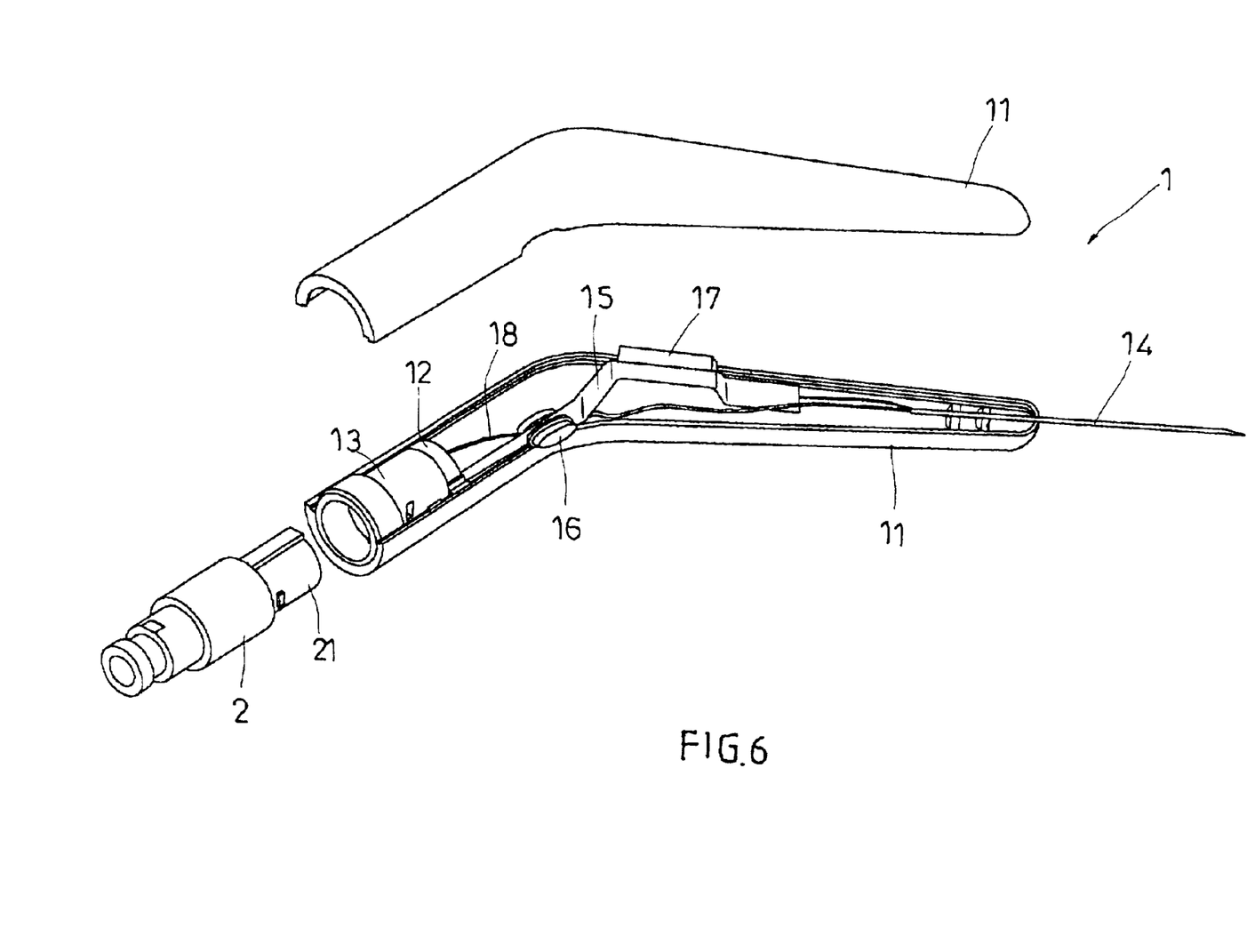
FIG. 6 is an exploded view of a disposable surgical device according to a second embodiment of the present invention.
Figure 7:
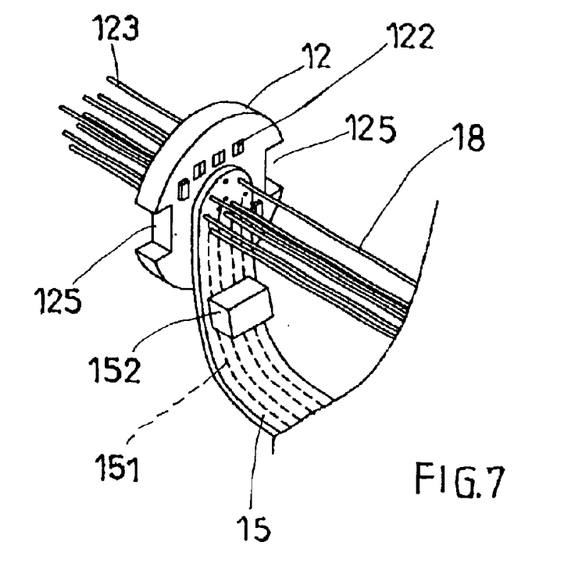
FIG. 7 is a perspective view of a part of the second embodiment of the present invention, showing the flex circuit termination connected to the smart block.

FIGS. 6 and 7 show a second embodiment of the present invention. According to this embodiment, electric wires 18 are provided to connect particular wire terminal points (solder points) 124 of the smart block 12 and the surgical tip 14 for transmission of high electric current, and the rest wire terminal points (solder points) 124 of the smart block 12 are respectively soldered to the corresponding wire terminal points (solder points) of the conductor lines 151 of the flex circuit termination 15.

Figure 8:
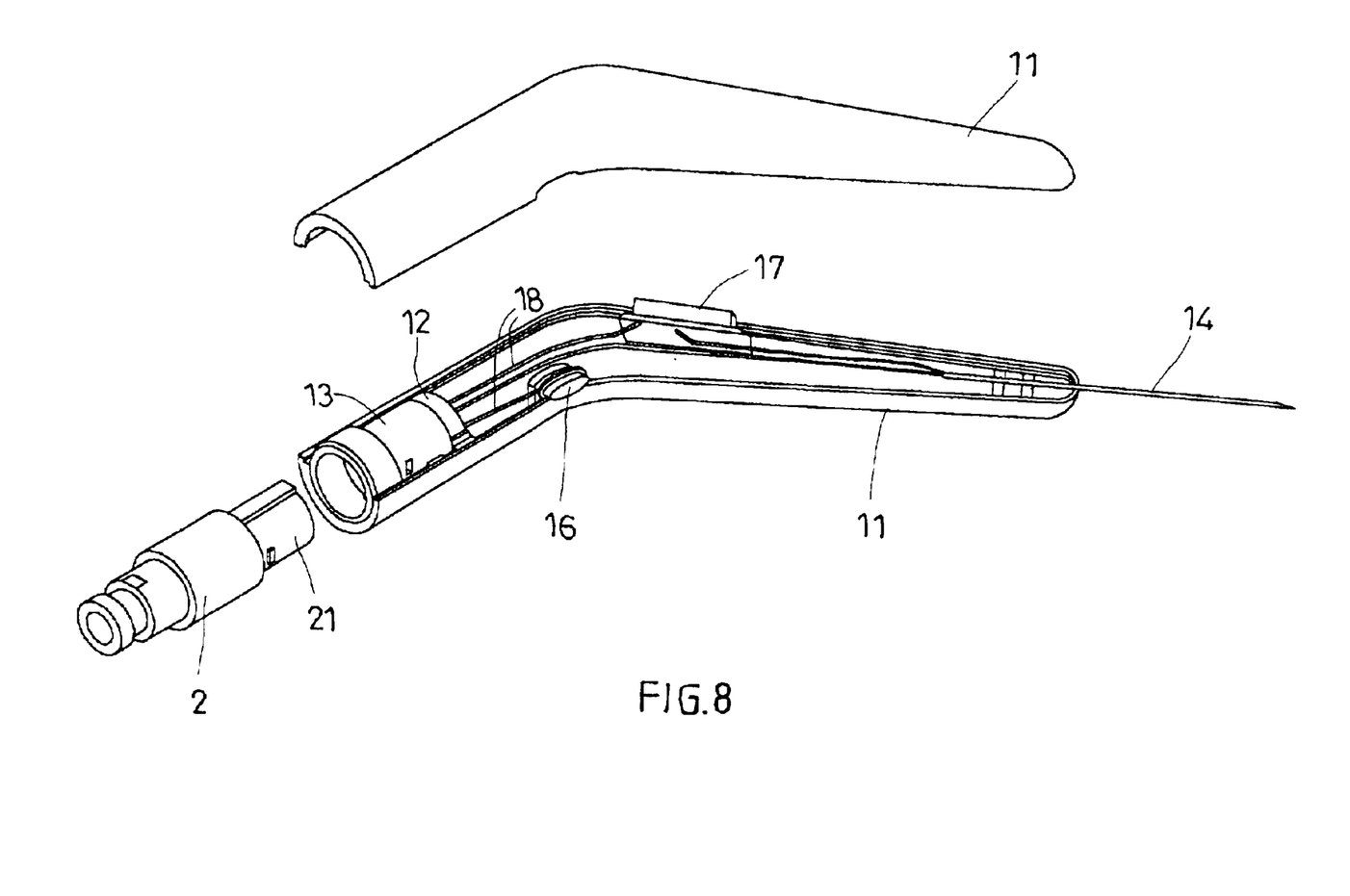
FIG. 8 is an exploded view of a disposable surgical device according to a third embodiment of the present invention.
Figure 9:
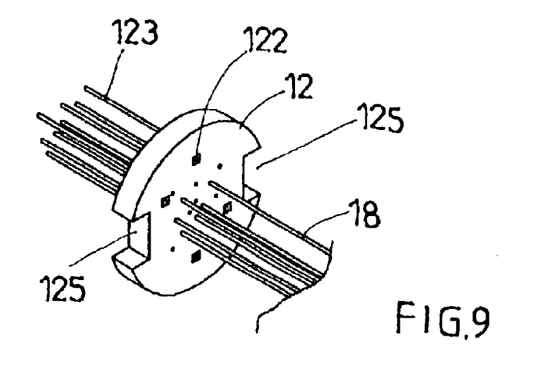
FIG. 9 is a perspective view of the smart block for the disposable surgical device according to the third embodiment of the present invention.

FIGS. 8 and 9 show a third embodiment of the present invention. According to this embodiment, electric wires 18 are installed in the smart block 12 and electrically connected between the wire terminal points (solder points) 124 of the smart block 12 and the surgical tip 14, i.e., all the wire terminal points (solder points) 124 of the smart block 12 are electrically connected to the surgical tip 14 by the electric wires 18 respectively for the transmission of high electric current.

A prototype of disposable surgical device has been constructed with the features of FIGS. 1~9. The disposable surgical device functions smoothly to provide all of the features discussed earlier.

Although particular embodiments of the invention have been described in detail for purposes of illustration, various modifications and enhancements may be made without departing from the spirit and scope of the invention. Accordingly, the invention is not to be limited except as by the appended claims.

What the invention claimed is:

1. A disposable surgical device comprising: a shell, said shell having a front side and a rear side; a smart block mounted in the rear side of said shell, said smart block comprising a circuit embedded therein, a plurality of electronic components mounted to the circuit of said smart block, a plurality of metal contact pins forwardly extended from a front side thereof and electrically connected to the circuit of said smart block and adapted for inserting into respective contact holes in the connector in the plug end of an industry standard connector interface to electrically connect said industry standard connector interface to the circuit of said smart block, a plurality of wire terminal points (solder points) provided at a rear side thereof and respectively electrically connected to said metal contact pins through the circuit of said smart block; a medical treatment terminal installed in the front side of said shell and adapted for performing surgery and treatments; and a flex circuit termination electrically connected between said smart block and said medical treatment terminal, said flex circuit termination comprising a plurality of conductor lines respectively connected to said medical treatment terminal, and wire terminal points respectively disposed at ends of said conductor lines and respectively soldered to the wire terminal points of said smart block.

2. The disposable surgical device as claimed in claim 1 further comprising a switch mounted to said flex circuit termination for power on/off control.

3. The disposable surgical device as claimed in claim 1 further comprising an indicator light mounted to said flex circuit terminal for status indication.

4. The disposable surgical device as claimed in claim 1 further comprising a socket provided in the rear end of said shell around the contact pins of said smart block, said socket comprising a socket hole disposed in a front side thereof and adapted for receiving the plug end of said industry standard connector interface, two retaining lugs bilaterally backwardly extended from a rear side thereof and respectively fastened to said smart block.

5. The disposable surgical device as claimed in claim 1, wherein said flex circuit termination has capacitor means and resistor means installed therein.

6. A disposable surgical device comprising: a shell, said shell having a front side and a rear side; a smart block mounted in the rear side of said shell, said smart block comprising a plurality of metal contact pins forwardly extended from a front side thereof and adapted for inserting into respective contact holes in the connector in the plug end of an industry standard connector interface, and a plurality of wire terminal points (solder points) provided at a rear side thereof and respectively electrically connected to said metal contact pin; a medical treatment terminal installed in the front side of said shell and adapted for performing surgery and treatments; and a flex circuit termination electrically connected between said smart block and said medical treatment terminal, said flex circuit termination comprising a plurality of conductor lines respectively connected to said medical treatment terminal, and wire terminal points respectively disposed at ends of said conductor lines and respectively connected to the wire terminal points of said smart block.

7. The disposable surgical device as claimed in claim 6 further comprising a switch mounted to said flex circuit termination for power on/off control.

8. The disposable surgical device as claimed in claim 6 further comprising an indicator light mounted to said flex circuit terminal for status indication.

9. The disposable surgical device as claimed in claim 6, wherein said flex circuit termination has capacitor means and resistor means installed therein.

10. The disposable surgical device as claimed in claim 6 further comprising a socket provided in the rear end of said shell around the contact pins of said smart block, said socket comprising a socket hole disposed in a front side thereof and adapted for receiving the plug end of said industry standard connector interface, two retaining lugs bilaterally backwardly extended from a rear side thereof and respectively fastened to said smart block.

11. A disposable surgical device comprising: a shell, said shell having a front side and a rear side; a smart block mounted in the rear side of said shell, said smart block comprising a circuit embedded therein, a plurality of electronic components mounted to the circuit of said smart block, a plurality of metal contact pins forwardly extended from a front side thereof and electrically connected to the circuit of said smart block and adapted for inserting into respective contact holes in the connector in the plug end of an industry standard connector interface to electrically connect said industry standard connector interface to the circuit of said smart block, a plurality of wire terminal points (solder points) provided at a rear side thereof and respectively electrically connected to said metal contact pins through the circuit of said smart block; a medical treatment terminal installed in the front side of said shell and adapted for performing surgery and treatments; a flex circuit termination electrically connected between said smart block and said medical treatment terminal, said flex circuit termination comprising a plurality of conductor lines electrically connected to said medical treatment terminal, and wire terminal points respectively disposed at ends of said conductor lines and selectively soldered to the wire terminal points of said smart block; and at least one electrical wire respectively selectively connected between the wire terminals of said smart block and said medical treatment terminal.

12. A disposable surgical device comprising: a shell, said shell having a front side and a rear side; a smart block mounted in the rear side of said shell, said smart block comprising a plurality of metal contact pins forwardly extended from a front side thereof and adapted for inserting into respective contact holes in the connector in the plug end of an industry standard connector interface, and a plurality of wire terminal points (solder points) provided at a rear side thereof and respectively electrically connected to said metal contact pin; a medical treatment terminal installed in the front side of said shell and adapted for performing surgery and treatments; a flex circuit termination electrically connected between said smart block and said medical treatment terminal, said flex circuit termination comprising a plurality of conductor lines electrically connected to said medical treatment terminal, and wire terminal points respectively disposed at ends of said conductor lines and selectively connected to the wire terminal points of said smart block; and at least one electrical wire respectively selectively connected between the wire terminals of said smart block and said medical treatment terminal.

13. A disposable surgical device comprising: a shell, said shell having a front side and a rear side; a smart block mounted in the rear side of said shell, said smart block comprising a circuit embedded therein, a plurality of electronic components mounted to the circuit of said smart block, a plurality of metal contact pins forwardly extended from a front side thereof and electrically connected to the circuit of said smart block and adapted for inserting into respective contact holes in the connector in the plug end of an industry standard connector interface to electrically connect said industry standard connector interface to the circuit of said smart block, a plurality of wire terminal points (solder points) provided at a rear side thereof and respectively electrically connected to said metal contact pins through the circuit of said smart block; a medical treatment terminal installed in the front side of said shell and adapted for performing surgery and treatments; and a plurality of electric wires electrically connected between said medical treatment terminal and the wire terminal points of said smart block.

\* \* \* \* \*